(12) United States Patent
Lorenz et al.

(10) Patent No.: US 6,538,150 B2
(45) Date of Patent: Mar. 25, 2003

(54) SUBSTITUTED SULFONYLAMINOMETHYLBENZOIC ACID (DERIVATIVES) AND THEIR PREPARATION

(75) Inventors: Klaus Lorenz, Weiterstadt (DE); Hans-Joachim Ressel, Hattersheim (DE); Lothar Willms, Hofheim (DE)

(73) Assignee: Aventis CropScience GmbH, Frankfurt (DE)

( * ) Notice: Subject to any disclaimer, the term of this patent is extended or adjusted under 35 U.S.C. 154(b) by 0 days.

(21) Appl. No.: 09/910,105

(22) Filed: Jul. 20, 2001

(65) Prior Publication Data

US 2002/0062029 A1 May 23, 2002

(30) Foreign Application Priority Data

Jul. 24, 2000 (DE) .......................... 100 36 184

(51) Int. Cl.[7] ............... C07C 205/00; C07C 321/00; C07C 315/00; A01N 47/36
(52) U.S. Cl. ................. 560/20; 560/8; 560/9; 560/19; 560/13; 562/426; 562/433; 562/430; 504/214
(58) Field of Search ............... 560/9, 8, 19, 20, 560/13; 562/426, 433, 430; 504/214

(56) References Cited

U.S. PATENT DOCUMENTS

| | | | |
|---|---|---|---|
| 4,372,778 A | | 2/1983 | Levitt |
| 5,463,081 A | | 10/1995 | Ort et al. |
| 5,648,315 A | | 7/1997 | Lorenz et al. |
| 5,719,532 A | * | 2/1998 | Nagata et al. |
| 5,925,596 A | | 7/1999 | Lorenz et al. |
| 6,221,809 B1 | | 4/2001 | Hacker et al. |

FOREIGN PATENT DOCUMENTS

| | | | |
|---|---|---|---|
| WO | WO 96/37485 | * | 11/1996 |
| WO | WO 00/44227 | | 8/2000 |

OTHER PUBLICATIONS

Gelb et al, J. Med. Chem. 1986, 29, pp 585–589.*
Dankwardt et al, Bioorg. Med. Chem. Lett., 1997, 7 (14) pp1921–1926.*
Saari et al, "A Convenient Synthesis of Nitro–Substituted 1,2–Benzisothiazol–3 (2$H$)–one 1,1 Dioxides (Nitrosaccharins)", J Heterocyclic Chem., 23, 1986, pp. 1253–1255, also referred to as XP–002178946.
U.S. patent application Ser. No. 09/353,701, Hacker et al., filed Jul. 14, 1999.
5–Agrochemicals; pp. 303–304, "Effects of Humactants on the Pesticide Uptake Through Plant Leaf Surfaces"; C. abstract only.
Chemische Berichte, 1957; 90. Jahrg; No. 6, pp. 841–1178.
J.Med. Chem. 1986, 29, 585–589, Gelb et al, "Substituted Isatoic Anhydrides:Selective Inactivators of Trypsin–like Serine Proteases".

* cited by examiner

Primary Examiner—Alan L. Rotman
Assistant Examiner—Héctor M Reyes
(74) Attorney, Agent, or Firm—Frommer Lawrence & Haug LLP

(57) ABSTRACT

The present invention relates to a compound of the formula (I)

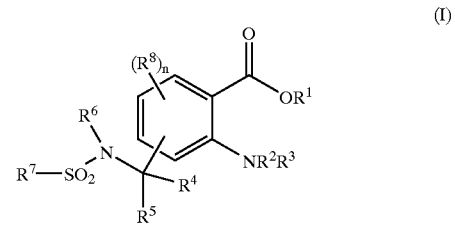

The compound according to the invention is suitable for the preparation of herbicidal active substances such as sulfonylureas.

9 Claims, No Drawings

SUBSTITUTED SULFONYLAMINOMETHYLBENZOIC ACID (DERIVATIVES) AND THEIR PREPARATION

The invention relates to the technical field of the intermediates for the preparation of active substances, in particular herbicidally active sulfonylureas.

It is known that aromatic amines can be reacted to give sulfonic acid derivatives such as sulfochlorides and further to give sulfonamides which, in turn, can be employed for the preparation of herbicidally active sulfonylureas (Meerwein et al., Chem. Berichte 90, 841–852 (1957) and EP-A-574418).

A substituted anthranilic acid is known from J. Med. Chem. 1986, Vol. 29, No. 4, page 585 as intermediate for the preparation of certain anhydrides which are suitable for inactivating trypsin-like enzymes.

It was an object to provide novel chemical compounds which are suitable for the preparation of herbicidally active sulfonylureas. Surprisingly, this object is achieved by compounds of the formula (I)

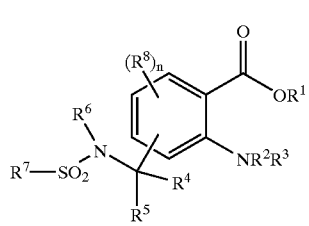

(I)

in which $R^1$ is H, $(C_1-C_8)$alkyl, $(C_3-C_8)$alkenyl or $(C_3-C_8)$alkynyl, where the last 3 radicals are unsubstituted or substituted, for example by one or more radicals selected from the group consisting of halogen, $(C_1-C_4)$alkoxy, $(C_1-C_4)$alkylthio, $[(C_1-C_4)$alkyl]carbonyl or $[(C_1-C_4)$alkoxy]carbonyl, $R^2$, $R^3$ independently of one another are H or acyl, preferably H, $R^4$, $R^5$ are H, $R^6$ is H or $(C_1-C_8)$alkyl which is unsubstituted or substituted, for example by one or more radicals selected from the group consisting of halogen, $(C_1-C_4)$alkoxy, $(C_1-C_4)$alkylthio, $(C_1-C_4)$alkylsulfinyl, $(C_1-C_4)$alkylsulfonyl, $[(C_1-C_4)$alkyl]carbonyl or CN, preferably H, $R^7$ is $(C_1-C_8)$alkyl, $(C_3-C_8)$alkenyl or $(C_3-C_8)$alkynyl which are unsubstituted or substituted, for example by one or more radicals selected from the group consisting of halogen, $(C_1-C_4)$alkoxy or $(C_1-C_4)$alkylthio, or $R^7$ is $(C_6-C_{14})$aryl (for example phenyl) which is unsubstituted or substituted, for example by one or more radicals selected from the group consisting of halogen, $NO_2$, CN, $(C_1-C_4)$alkyl, $(C_1-C_4)$haloalkyl or $(C_1-C_4)$alkoxy, or $R^7$ is mono- or di-$(C_1-C_8)$alkylamino which is unsubstituted or substituted, for example by one or more radicals selected from the group consisting of halogen, $(C_1-C_4)$alkoxy, $(C_1-C_4)$alkylthio, $(C_1-C_4)$alkylsulfinyl, $(C_1-C_4)$alkylsulfonyl, $[(C_1-C_4)$alkyl]carbonyl, $[(C_1-C_4)$alkoxy]carbonyl or CN, or $R^6$ and $R^7$ together form a chain of the formula $—(CH_2)_m B_{m1}—$ which is unsubstituted or substituted, for example by one or more $(C_1-C_4)$alkyl radicals, and where m=2, 3 or 4, $m^1=0$ or 1 and B=CO or $SO_2$, $R^8$ radicals, are identical or different and are $(C_1-C_4)$alkyl, $(C_1-C_4)$alkoxy, $[(C_1-C_4)$alkyl]carbonyl or $[(C_1-C_4)$alkoxy]carbonyl which are unsubstituted or substituted, for example by one or more radicals selected from the group consisting of halogen, $(C_1-C_4)$alkoxy, $(C_1-C_4)$alkylthio, $[(C_1-C_4)$alkyl]carbonyl or $[(C_1-C_4)$alkoxy]carbonyl, or $R^8$ is halogen or $NH_2$, and n is 0, 1, 2 or 3, preferably 0.

Preferred compounds of the formula (I) are those in which $R^1$ is H or $(C_1-C_4)$alkyl, preferably $(C_1-C_4)$alkyl, $R^2$ and $R^3$ are H, $R^4$ and $R^5$ are H, $R^6$ is H, $R^7$ is $(C_1-C_4)$alkyl, and n is 0.

Compounds of the formula (I) which are of particular importance are those in which the group $CR^4R^5$—$NR^6$—$SO_2$—$R^7$ is in the para position relative to the group —CO—$OR^1$. If together form a chain of the formula $—(CH_2)_m B_{m1}—$ and $m^1=1$, it is preferable that B is bound to the nitrogen atom which has $R^6$ attached to it.

Examples of compounds of the formula (I) are listed in table 1 hereinbelow:

TABLE 1

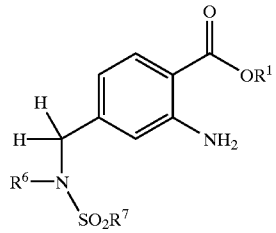

(Ia)

| Compound | $R^1$ | $R^6$ | $R^7$ |
|---|---|---|---|
| 1 | Me | H | Me |
| 2 | Me | Me | Me |
| 3 | Me | H | NHMe |
| 4 | Me | Me | NHMe |
| 5 | Me | H | N(Me)$_2$ |
| 6 | Me | Me | N(Me)$_2$ |
| 7 | Me | —CH$_2$—CH$_2$—CH$_2$— | |
| 8 | Me | —CH$_2$—CH$_2$—CH$_2$—CH$_2$— | |
| 9 | Me | H | Phe |
| 10 | Me | Me | Phe |
| 11 | Me | H | CH$_2$F |
| 12 | Me | Me | CH$_2$F |
| 13 | Me | H | CF$_3$ |
| 14 | Me | Me | CF$_3$ |
| 15 | Me | H | Et |
| 16 | Me | Me | Et |
| 17 | Me | H | nPr |
| 18 | Me | Me | nPr |
| 19 | Me | H | iPr |
| 20 | Me | Me | iPr |
| 21 | Me | H | nBu |
| 22 | Me | Me | nBu |
| 23 | Me | Et | Me |
| 24 | Me | Et | Et |
| 25 | Me | Et | NHMe |
| 26 | Me | Et | N(Me)$_2$ |
| 27 | Me | Et | Phe |
| 28 | Me | Et | CH$_2$F |
| 29 | Me | Et | CF$_3$ |
| 30 | Me | Et | nPr |
| 31 | Me | Et | iPr |
| 32 | Me | Et | nBu |
| 33 | Et | H | Me |

TABLE 1-continued (Ia)

| Compound | R¹ | R⁶ | R⁷ |
|---|---|---|---|
| 34 | Et | Me | Me |
| 35 | Et | H | NHMe |
| 36 | Et | Me | NHMe |
| 37 | Et | H | N(Me)₂ |
| 38 | Et | Me | N(Me)₂ |
| 39 | Et | —CH₂—CH₂—CH₂— | |
| 40 | Et | —CH₂—CH₂—CH₂—CH₂— | |
| 41 | Et | H | Phe |
| 42 | Et | Me | Phe |
| 43 | Et | H | CH₂F |
| 44 | Et | Me | CH₂F |
| 45 | Et | H | CF₃ |
| 46 | Et | Me | CF₃ |
| 47 | Et | H | Et |
| 48 | Et | Me | Et |
| 49 | Et | H | nPr |
| 50 | Et | Me | nPr |
| 51 | Et | H | iPr |
| 52 | Et | Me | iPr |
| 53 | Et | H | nBu |
| 54 | Et | Me | nBu |
| 55 | Et | Et | Me |
| 56 | Et | Et | Et |
| 57 | Et | Et | NHMe |
| 58 | Et | Et | N(Me)₂ |
| 59 | Et | Et | Phe |
| 60 | Et | Et | CH₂F |
| 61 | Et | Et | CF₃ |
| 62 | Et | Et | nPr |
| 63 | Et | Et | iPr |
| 64 | Et | Et | nBu |

In table 1, Me = methyl, Et = ethyl, nPr = n-propyl, iPr = isopropyl, nBu = n-butyl, Phe = phenyl.

If the term acyl is used in the present description, it denotes the radical of an organic acid which arises formally by eliminating an OH group from the organic acid, for example the radical of a carboxylic acid and radicals of acids derived therefrom, such as thiocarboxylic acid, optionally N-substituted iminocarboxylic acids or the radicals of carbonic monoesters, optionally N-substituted carbamic acids, sulfonic acids, sulfinic acids, phosphonic acids, phosphinic acids.

An acyl radical is preferably formyl or acyl from the group consisting of CO—$R^x$, CS—$R^x$, CO—$OR^x$, CS—$OR^x$, CS—$SR^x$, $Cr^x$=$NR^Y$, $SOR^Y$ or $SO_2^Y$, where $R^x$ and $R^Y$ are each a $C_1$–$C_{10}$-hydrocarbon radical such as $C_1$–$C_{10}$-alkyl or $C_6$–$C_{10}$-aryl, each of which is unsubstituted or substituted, for example by one or more substituents selected from the group consisting of halogen such as F, Cl, Br, I, alkoxy, haloalkoxy, hydroxyl, amino, nitro, cyano or alkylthio, or acyl is aminocarbonyl or aminosulfonyl, the two last-mentioned radicals being unsubstituted, N-monosubstituted or N,N-disubstituted, for example by substituents from the group consisting of alkyl or aryl. Acyl is, for example, formyl, haloalkylcarbonyl, alkylcarbonyl such as ($C_1$–$C_4$)alkylcarbonyl, phenylcarbonyl, it being possible for the phenyl ring to be substituted, or alkyloxycarbonyl, such as ($C_1$–$C_4$) alkyloxycarbonyl, phenyloxycarbonyl, benzyloxycarbonyl, alkylsulfonyl, such as ($C_1$–$C_4$) alkylsulfonyl, alkylsulfinyl, such as $C_1$–$C_4$ (alkylsulfinyl), N-alkyl-1-iminoalkyl, such as N—($C_1$–$C_4$)-1-imino-($C_1$–$C_4$)alkyl and other radicals of organic acids.

In formula (I) and the general formulae used hereinbelow, the radicals alkyl, alkoxy, haloalkyl, haloalkoxy and alkylthio and the corresponding substituted radicals can be in each case straight-chain or branched in the carbon skeleton. Unless specified otherwise, the lower carbon skeletons, for example those having 1 to 4 carbon atoms, are preferred amongst these radicals. Alkyl radicals, also in the composite meanings such as alkoxy, haloalkyl and the like, are, for example, methyl, ethyl, n- or i-propyl, n-, i-, t- or 2-butyl, pentyls, hexyls such as n-hexyl, i-hexyl and 1,3-dimethylbutyl, heptyls such as n-heptyls, 1-methylhexyl and 1,4-dimethylpentyl; alkenyl and alkynyl radicals have the meanings of the possible unsaturated radicals which correspond to the alkyl radicals; for example alkenyl is allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, propargyl, but-2-yn-1-yl, but-3-yn-1-yl, 1-methylbut-3-yn-1-yl.

Alkenyl, for example in the form "($C_3$–$C_8$)alkenyl", is preferably an alkenyl radical having 3 to 8 carbon atoms in which the double bond is not positioned at the carbon atom which is linked to the remaining moiety of the compound (I) ("yl" position). This also applies analogously to alkynyl radicals.

Halogen is, for example, fluorine, chlorine, bromine or iodine. Haloalkyl, -alkenyl and -alkynyl are alkyl, alkenyl or alkynyl, each of which is partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl_2$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this also applies analogously to haloalkenyloxy and other halogen-substituted radicals.

Substituted radicals such as substituted hydrocarbon radicals, for example substituted alkyl, alkenyl, alkynyl, aryl, for example phenyl, are, for example, a substituted radical which is derived from the unsubstituted skeleton, the substituents being, for example, one or more, preferably 1, 2 or 3, radicals selected from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino such as acylamino, mono- and dialkylamino, and alkylsulfinyl, haloalkylsulfinyl, alkylsulfonyl, haloalkylsulfonyl and, in the case of cyclic radicals, also alkyl and haloalkyl, and unsaturated aliphatic radicals which correspond to the abovementioned saturated hydrocarbon-containing radicals, such as alkenyl, alkynyl, alkenyloxy, alkynyloxy and the like. In the case of radicals with carbon atoms, those having 1 to 4 carbon atoms, in particular 1 or 2 carbon atoms, are preferred. Preferred are, as a rule, substituents selected from the group consisting of halogen, for example fluorine and chlorine, ($C_1$–$C_4$)alkyl, preferably methyl or ethyl, ($C_1$–$C_4$) haloalkyl, preferably trifluoromethyl, ($C_1$–$C_4$)alkoxy, preferably methoxy or ethoxy, ($C_1$–$C_4$)haloalkoxy, nitro and cyano. Especially preferred in this context are substituents methyl, methoxy and chlorine.

Optionally substituted phenyl or phenoxy is preferably phenyl or phenoxy, each of which is unsubstituted or monoor polysubstituted, preferably up to trisubstituted, by identical or different radicals selected from the group consisting of halogen, $(C_1-C_4)$alkyl, $(C_1-C_4)$alkoxy, $(C_1-C_4)$haloalkyl, $(C_1-C_4)$haloalkoxy and nitro, for example o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

If substitutions are defined by one or more radicals from among a group of radicals, this encompasses both the substitution by one or more identical radicals and the mono- or polysubstitution by different radicals.

Subject of the invention are also all stereoisomers which are encompassed by formula (I) and their mixtures. Such compounds of the formula (I) contain one or more asymmetric carbon atoms which are not indicated separately in formula (I). The possible stereoisomers which are defined by their specific spatial shape, such as enantiomers or diastereomers, are all encompassed by formula (I) and can be obtained from mixtures of the stereoisomers by customary methods or else by stereoselective reactions in combination with the use of stereochemically pure starting materials. Formula (I) also encompasses tautomers of the compounds stated, inasfar as they are formed by proton migration and are chemically stable.

The compounds of the formula (I) may form salts in which an acidic hydrogen atom is replaced by a suitable cation. These salts are, for example, metal salts; preferably alkali metal salts or alkaline earth metal salts, in particular sodium salts and potassium salts, or else ammonium salts or salts of organic amines. Likewise, salt formation can be effected by an addition reaction of an acid with basic groups, such as amino. Acids which are suitable for this purpose are strong inorganic and organic acids, for example HCl, HBr, $H_2SO_4$, $HNO_3$ or formic acid.

Compounds of the formula (I) are successfully synthesized in very good yields and purities starting from compounds of the formula (II) mentioned hereinbelow.

Subject of the present invention is thus also a process for the preparation of compounds of the formula (I) comprising the steps of 1a) reacting a compound of the formula (II)

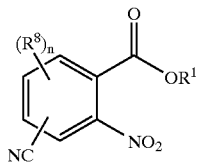
(II)

by catalytic hydrogenation in the absence of an acid to give a compound of the formula (III) or by catalytic hydrogenation in the presence of an acid, for example $H^+X^-$, where $X^-$ is an equivalent of an acid anion, such as halogen, for example $Cl^-$, $Br^-$ or $I^-$, or $HSO_4^-$, $½SO_4^{2-}$, $H_2PO_4^-$, $½HOP_4^{2-}$, $⅓PO_4^{3-}$ or $^-OCOR$ (where R=H or $(C_1-C_8)$alkyl) to give a compound of the formula (IIIa), where $X^-$ is an equivalent of an acid anion, such as halide, for example $Cl^-$, $Br^-$ or $I^-$, or $HSO_4^-$, $½SO_4^{2-}$, $H_2PO_4^-$, $½HPO_4^{2-}$, $⅓PO_4^{3-}$ or $^-OCOR$ (where R=H or $(C_1-C_8)$alkyl),

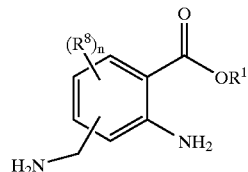
(III)

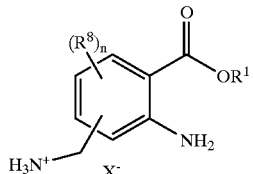
(IIIa)

and subsequently 1b) reacting the compound of the formula (III) or (IIIa) with a sulfonic acid derivative to give a compound of the formula (I) where $R^2$, $R^3$ and $R^6$=H; or 2a) α) reacting a compound of the formula (II)

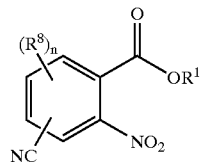
(II)

by customary reduction methods for nitro compounds to give a compound of the formula (IV),

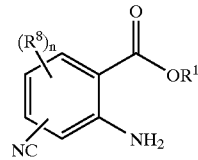
(IV)

and subsequently

β) reacting the compound of the formula (IV) either by catalytic hydrogenation or by customary reduction methods for nitriles to give a compound of the formula (III) or (IIIa), and subsequently 2b) reacting the compound of the formula (III) or (IIIa) with a sulfonic acid derivative to give a compound of the formula (I) where $R^2$, $R^3$ and $R^6$=H; or 3a) α) reacting a compound of the formula (II)

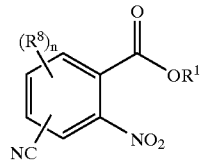
(II)

by customary reduction methods for nitrites to give a compound of the formula (V) or (Va), where $X^{\ominus}$ is as defined in formula (IIIa),

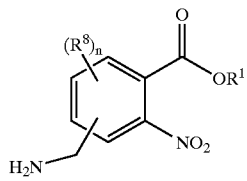
(V)

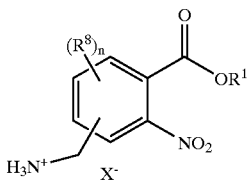
(Va)

and subsequently

β) reacting the compound of the formula (V) or (Va) by customary reduction methods for nitro compounds or by catalytic hydrogenation to give a compound of the formula (III) or (IIIa), and subsequently 3b) reacting the compound of the formula (III) or (IIIa) with a sulfonic acid derivative to give a compound of the formula (I) where $R^2$, $R^3$ and $R^6$=H; or 4a) α) reacting a compound of the formula (II)

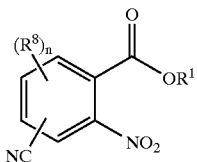
(II)

by customary reduction methods for nitrites to give a compound of the formula (V) or (Va), where $X^-$ is as defined in formula (IIIa),

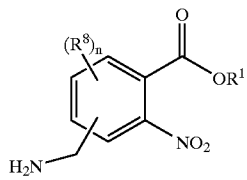
(V)

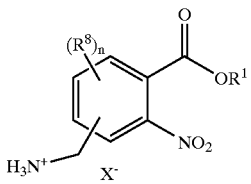
(Va)

β) and subsequently reacting the compound of the formula (V) or (Va) with a sulfonic acid derivative to give a compound of the formula (VI),

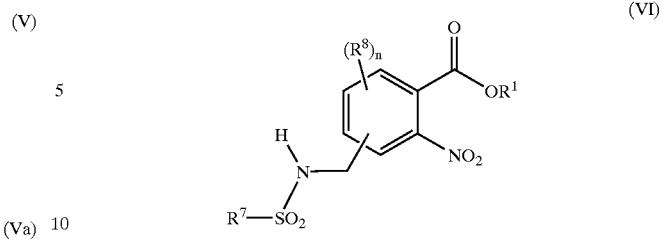
(VI)

and subsequently 4b) reacting the compound of the formula (VI) by customary reduction methods for nitro compounds or by catalytic hydrogenation to give a compound of the formula (I) where $R^2$, $R^3$ and $R^6$=H.

The compounds of formulae (III), (IIIa), (V), (Va) and (VI) are novel and also subject of the present invention.

Compounds of the formula (I) where $R^2$ and/or $R^3$=acyl can be obtained by acylating compounds of the formula (I) where $R^2$ and $R^3$=H with acylating agents such as carbonyl halides, sulfonyl halides and carbamoyl halides, carboxylic anhydrides, sulfonic anhydrides, haloformic esters or isocyanates, by customary methods (see, for example, L.-F. Tietze, Th. Eicher, Reaktionen und Synthesen im organisch-chemischen Praktikum [Reactions and Syntheses in the Organochemical Laboratory Practical], Thieme Verlag Stuttgart/New York, 1981, pp. 131, 316, 318, 345; R. C. Larock, Comprehensive Organic Transformations (1989), pp. 979, 981). Examples of suitable solvents are aprotic solvents such as dichloromethane, acetonitrile, dioxane, tetrahydrofuran, toluene or chlorobenzene, preferably at temperatures of from 0° C. to the boiling point of the solvent.

Compounds of the formula (I) where $R^6$=unsubstituted or substituted $C_1$–$C_8$-alkyl can be obtained for example by alkylating compounds of the formula (I) where $R^6$=H with alkylating agents such as alkyl halides, alkyl sulfates such as dimethyl sulfate or alkyl tosylates by customary methods. Examples of suitable solvents are acetone and dimethylformamide (cf., for example, R. C. Larock, Comprehensive Organic Transformations (1989), p. 398; L.-F. Tietze, Th. Eicher, Reaktionen und Synthesen im organisch-chemischen Praktikum, Thieme Verlag Stuttgart/New York, 1981, p. 75; Organikum, Organisch-chemisches Grundpraktikum [Basic Laboratory Practical in Organic Chemistry] VEB, Berlin 1981). The alkylation can be carried out in the presence of bases such as $K_2CO_3$, NaH or alkoxides such as sodium alkoxide. The starting material is preferably compounds of the formula (I) in which $R^2$ and $R^3$ are acyl.

Compounds of the formula (I) where $R^6$=unsubstituted or substituted $C_1$–$C_8$-alkyl can also be obtained for example via reductive aminations, for example with aldehydes or ketones in the presence of reducing agents such as $H_2$/catalyst, formic acid, zinc/HCl, sodium borohydride or sodium cyanoborohydride. An example is the Leuckard-Wallach reaction with formaldehyde and formic acid.

Preferred processes are those in which the nitro and the nitrile group in compounds of the formula (II) are reduced jointly in one process step by means of catalytic hydrogenation in accordance with process variant 1a) to give compounds of the formula (III) or (IIIa).

The amino compounds of the formulae (III) and (V) which are obtained as intermediates in the process according to the invention can also arise in the form of their salts (IIIa) and (Va) and can be reacted further when the reaction or work-up is effected in an acidic medium.

The symbols given in formulae (II), (III), (IIIa), (IV), (V), (Va) and (VI) have the same meaning as in formula (I), including the preferred ranges mentioned herefor. Preferred compounds of the formulae (II), (III), (IIIa), (IV), (V), (Va) and (VI) are those in which the groups —CN (formulae (II) and (IV)), —$CH_2$—$NH_2$ (formulae (III) and (V)), —$CH_2$—$NH_3^+X^-$ (formulae (IIIa) and (Va)) and —$CH_2$—$NR^6$—$SO_2$—$R^7$ (formula (VI)) are in the para position relative to the group —CO—$OR^1$.

Furthermore, substeps of the process according to the invention are also subject of the invention.

The compounds of the formula (II) are known, cf., for example, DE 22 39 799 C3 or Journal of the American Chemical Society 99, 6721 (1977).

The catalytic hydrogenation of the compound of the formula (II) by process variant 1a), of the compound of the formula (IV) by process variant 2aβ), of the compound of the formula (V) or (Va) by process variant 3aβ) or of the compound of the formula (VI) by process variant 4b) is successfully carried out by means of customary hydrogenation methods. Examples of hydrogen sources which can be used are hydrogen gas, hydrazine or HN=NH. Particularly suitable hydrogenation catalysts are noble-metal catalysts, for example Pd, Pt, Rh, Ir or Ni or Co catalysts. The noble metals can be used in elemental form or in the form of oxides or halides. The noble-metal catalysts can be used as desired without or, preferably, with support materials such as active charcoal, kieselguhr, silicates.

The hydrogenation can be carried out both by atmospheric pressure and by applying a superatmospheric hydrogen pressure, as a rule between 1 and 100 bar, preferably 1–50 bar. In general, the suitable temperature is in the range of from –20 to 150° C., preferably between 0 and 120° C.

Examples of solvents which are suitable for the hydrogenation are solvents of the groups water, alcohols such as methanol or ethanol, ethers such as diethyl ether, tetrahydrofuran or dioxane, amides such as dimethylformamide or dimethylacetamide, esters such as ethyl acetate, organic carboxylic acids such as formic acid or acetic acid, aromatic hydrocarbons such as toluene, xylene and chlorobenzene, or halogenated aliphatic hydrocarbons such as $CH_2Cl_2$, it being possible to employ the solvents in pure form or as mixtures.

The catalytic hydrogenation of the compounds of the formula (II) by process variant 1a) or of the compounds of the formula (IV) by process variant 2aβ) is preferably carried out in the presence of 1–10 molar equivalents of an acid. Solvents which are preferably used are alcohols such as methanol or ethanol, or water. Examples of suitable acids are inorganic acids or carboxylic acids. Preferred are acids of the formula $H^+X^-$ where $X^-$ is an equivalent of an acid moiety, such as halogen for example $Cl^-$, $Br^-$ or $I^-$, or $HSO_4^-$, $½SO_4^{2-}$, $H_2PO_4^-$, $½HPO_4^{2-}$, $⅓PO_4^{3-}$ or $^-OCOR$ (where R=H or ($C_1$–$C_8$)alkyl), for example hydrohalic acids such as hydrochloric acid or hydrobromic acid, or sulfuric acid, phosphoric acid, formic acid or acetic acid. If, for example, the two last-mentioned acids are used, the acids may also fully assume the role of the solvent.

The catalytic hydrogenation of the compounds of the formula (IV) can also be carried out by using 1–10 molar equivalents of ammonia, nickel or cobalt catalysts such as Raney nickel or Raney cobalt preferably being employed. Solvents which are preferably used in this context are alcohols such as methanol or ethanol.

The reduction of the nitro group in compounds of the formula (II) by process variant 2aα), compounds of the formulae (V) and (Va) by process variant 3aβ) or compounds of the formula (VI) by process variant 4b) can be carried out with customary reducing agents for aromatic nitro compounds. Such reducing agents and reaction conditions are described, for example, in R. C. Larock, Comprehensive Organic Transformations (1989) pp. 411–415, VCH Publishers Inc. and the literature cited therein. Examples of preferred reducing agents are Fe, Zn, Sn or their salts such as $FeSO_4$ or Sn-II salts such as $SnCl_2$. Examples of suitable solvents are organic carboxylic acids, alcohols and/or mineral acids. In general, the reaction temperature is between 0° C. and the boiling point of the solvent.

The reduction of the nitrile group in compounds of the formula (IV) by process variant 2aβ) and compounds of the formula (II) by process variant 3aα) and 4aα) can be carried out by customary reducing agents for nitrites. Such reducing agents and reaction conditions are described, for example, in R. C. Larock, Comprehensive Organic Transformation (1989) pp. 437–438, VCH Publishers Inc. and the literature cited therein. Examples of preferred reducing agents are boron hydride compounds or aluminum hydride compounds such as $BH_3$/THF, $BH_3$/DMS and their salts such as $NaBH_4$. Examples of suitable solvents are ethers such as dioxane or tetrahydrofuran. The reaction temperature is generally between 0° C. and the boiling point of the solvent. If the reduction product is subsequently worked up in an acid medium, for example methanol/HCl, the compound of the formula (III) (process variant 2aβ) or the compound of the formula (V) (process variants 3aα and 4aα) can be obtained in the form of a salt of the formula (IIIa) or (Va), respectively, which can be reacted further analogously to compound (III) or compound (V), respectively.

The acylation of the compounds of the formula (III) or (IIIa) by process variant 1b), 2b) or 3b) or of the compounds of the formula (V) or (Va) by process variant 4aβ) with a sulfonic acid derivative can be carried out under customary conditions for acylation reactions to give the compounds of the formula (VI) in the case of compounds of the formula (V) or (Va) or to give the compounds of the formula (I) according to the invention in the case of compounds of the formula (III) or (IIIa).

For example, compounds of the formula (III) or (IIIa), or (V) or (Va), are reacted in suitable solvents with sulfonic acid derivatives in the presence of bases as acid acceptors to give compounds of the formula (I) or (VI) respectively. Examples of solvents which are suitable for the acylations are solvents from the groups water, alcohols such as methanol or ethanol, halogenated aliphatic hydrocarbons such as $CH_2Cl_2$, aromatic hydrocarbons such as toluene, chlorobenzene or xylene, ethers such as diethyl ether, tetrahydrofuran or dioxane, ketones such as acetone or methyl isobutyl ketone, esters such as ethyl acetate, and aprotic solvents such as acetonitrile, dimethylformamide or dimethylacetamide, it being possible for the solvents to be employed in pure form or as mixtures. Preferred are water and mixtures of water and water-soluble organic solvents from the abovementioned groups.

Bases which are suitable are inorganic or organic bases, for example carbonates such as $K_2CO_3$, $Na_2CO_3$ or $NaHCO_3$, alkali metal hydroxides and alkaline earth metal hydroxides such as NaOH, KOH or $Ca(OH)_2$, or amines such as triethylamine. In general, the bases are employed in amounts of 1–10 molar equivalents, preferably 1–5 molar equivalents, per compound of the formula (III) or (V); when compounds of the formula (IIIa) or (Va) are employed, the minimum amount of the base employed is at least two molar equivalents.

Examples of suitable sulfonic acid derivatives are sulfonyl halides such as fluorides, chlorides, bromides or iodides, and sulfonic anhydrides. Preferred are sulfonic acid derivatives of the formula $R^7$—$SO_2$—Z, where $R^7$ is defined as in formula (I), and Z is a leaving group such as halogen (for example fluorine, chlorine, bromine or iodine) or O—$SO_2$—$R^Z$, where $R^Z$ is as defined for $R^7$ in formula (I). The acylation is carried out for example in such a way that the compounds of the formula (III) or (IIIa), or (V) or (Va), are reacted with the sulfonic acid derivatives in suitable solvents in the presence of a suitable base, in general at temperatures of from −20 to 100° C. Preferred are temperatures of from −10 to 50° C. The amounts of sulfonic acid derivatives are generally 1–10 molar equivalents, preferably 1–5 molar equivalents, per compound of the formula (III) or (IIIa), or (V) or (Va).

In addition to compounds of the formula (I) and their preparation, the present invention also relates to their further reaction to give compounds of the formulae (VII) and (VIII). To do this, compounds of the formula (I) where $R^2$ and/or $R^3$=acyl must first be converted by customary methods into compounds of the formula (I) where $R^2$=$R^3$=H, and these are then further reacted to give compounds of the formulae (VII) and (VIII). The symbols used in formulae (VII) and (VIII) have the same meanings as stated for formula (I), including the preferred ranges stated herefor, and Y in formula (VII) is halogen such as fluorine, chlorine, bromine or iodine. Preferred compounds of the formulae (VII) and (VIII) are those in which the group —$CH_2$—$NR^6$—$SO_2$—$R^7$ is in the para position relative to the group —CO—$OR^1$.

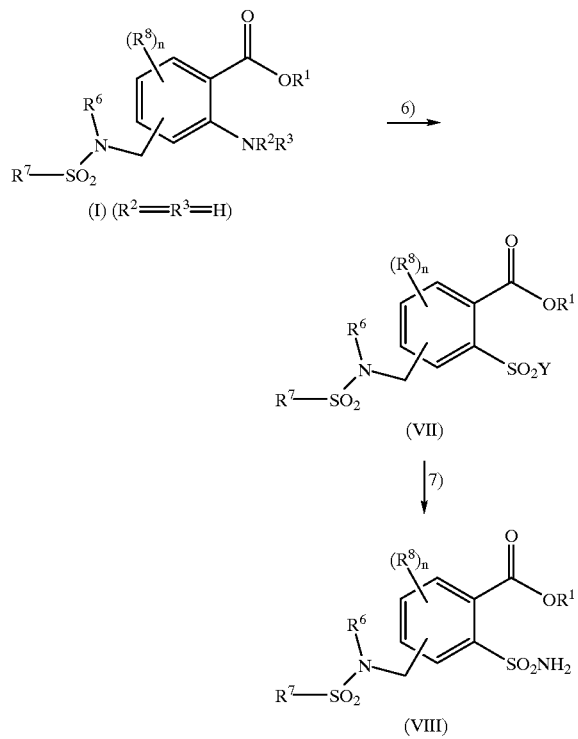

As is described in (EP-A-723 534), compounds of the formulae (VII) and (VIII) are suitable precursors for the preparation of potent herbicidal sulfonylureas, the preparation of the compounds of the formulae (VII) and (VIII) being especially efficient in the present process according to the invention and the compounds of the formulae (VII) and (VIII) being obtained in very good yields and purities.

Methods for the conversion 6) of anilines into sulfonyl halides are known (see, for example, H. Meerwein et al., Chem. Berichte 90, 841–852 (1957)). Surprisingly, compounds of the formula (I) where $R^2$, $R^3$=H are successfully reacted to give compounds of the formula (VII) on the basis of procedures described in the literature. Thus, compounds of the formula (I) where $R^2$, $R^3$=H can be diazotized under suitable conditions and subsequently coupled with suitable $SO_2$ sources, such as $SO_2$ gas, $Na_2S_2O_5$ or $NaHSO_3$ in the presence of acids such as carboxylic acids, for example acetic acid, or inorganic acids, for example hydrohalic acids HY such as HCl or HBr, and catalysts, for example copper catalysts based on Cu(I) and/or Cu(II) salts to give sulfonyl halides of the formula (VII).

The diazotization can be carried out with suitable diazotizing agents such as $NaNO_2$ in the presence of acids such as inorganic acids, preferably hydrohalic acids HY, such as HCl or HBr. The solvent used is preferably a water/acid mixture, in particular a mixture of water/carboxylic acid (for example acetic acid) or water/mineral acid (for example hydrohalic acid HY such as HCl or HBr). In general, the reaction temperature is −20 to 50° C., preferably −10 to 20° C.

The following are examples which can be used as solvents for the subsequent coupling reaction: water, carboxylic acids such as acetic acid, carboxylic esters such as ethyl acetate, ethers such as diethyl ether, tetrahydrofuran or dioxane, halogenated aliphatic hydrocarbons such as $CH_2Cl_2$ or dichloroethane, aromatic hydrocarbons such as toluene, chlorobenzene or xylene, or ketones such as acetone or methyl isobutyl ketone. Moreover, the reaction mixture contains acids, for example carboxylic acids such as acetic acid or mineral acids such as hydrohalic acids HY, for example HCl or HBr, which are either still present from the diazotization reaction and/or are added when the coupling reaction is carried out. Examples of $SO_2$ sources which can be used are, for example, $SO_2$ gas (1–10 equivalents), $Na_2S_2O_5$ (1–10 equivalents) or $NaHSO_3$ (1–10 equivalents), in the presence of catalysts, for example copper catalysts such as CuCl (1–20 mol %), $CuCl_2$ (1–20 mol %), CuBr (1–20 mol %) or $CuBr_2$ (1–20 mol %).

Starting from sulfonyl halides of the formula (VII) the aminolysis 7) which yields sulfonic amides of the formula (VIII) is, surprisingly, successfully carried out with high efficiency and in high yields by reacting compounds of the formula (VII) for example in suitable solvents with ammonia.

The aminolysis can be carried out with suitable reagents, for example 2–10 molar equivalents of aqueous ammonia solution or $NH_3$ gas in the presence of a solvent, for example ketones such as acetone or methyl isobutyl ketone, halogenated aliphatic hydrocarbons such as $CH_2Cl_2$, aromatic hydrocarbons such as xylene, toluene or chlorobenzene, ethers such as diethyl ether, tetrahydrofuran or dioxane, esters such as ethyl acetate, aprotic solvents such as dimethylformamide, dimethylacetamide or acetonitrile, or mixtures of these solvents. In general, the reaction temperature is from −10 to 100° C., preferably −10 to 40° C., especially preferably −10 to 20° C.

The compounds of the formulae (VII) and (VIII) can subsequently be reacted in various ways to give sulfonylureas, preferably sulfonylureas of the formula (XIII) and/or their salts, for example by 8) reacting a sulfonyl halide of the formula (VII) with a cyanate MOCN, in which M is an ammonium ion or an alkali metal ion such as Li, Na or K, and with an amino heterocycle of the formula (XII) in the presence of a base to give the sulfonylurea; or

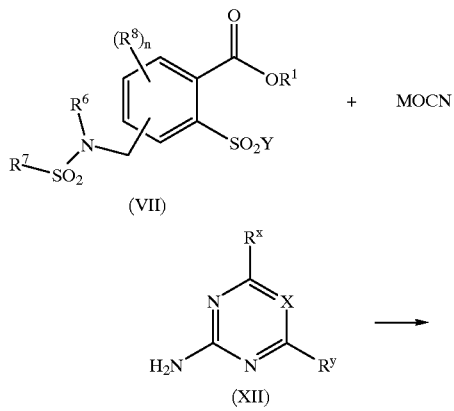

(VII)

(XII)

(XIII)

9) reacting a compound of the formula (VIII) with a heterocyclic carbamate of the formula (IX), in which Ph is unsubstituted or substituted phenyl to give the sulfonylurea; or

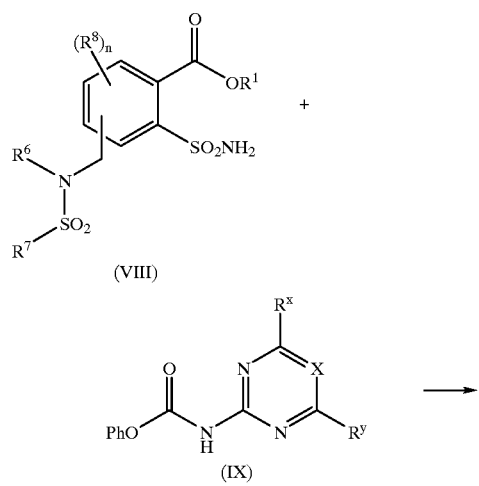

(VIII)

(IX)

(XIII)

10) a) first reacting an amino heterocycle of the formula (XII) in the presence of a base such as trialkylamine, for example triethylamine, with phosgene to give a heterocyclyl isocyanate of the formula (X), and b) reacting the heterocyclyl isocyanate formed, of the formula (X), with a phenylsulfonamide of the formula (VIII) to give the sulfonylurea; or

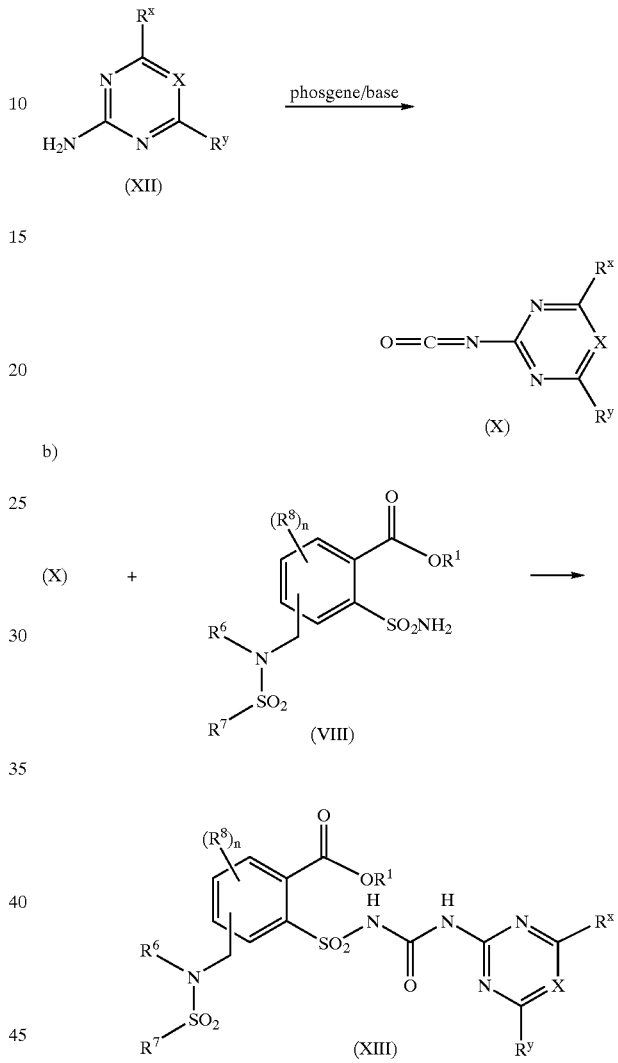

(XII)

(X)

(VIII)

(XIII)

11) a) reacting a compound of the formula (VIII) with an alkyl isocyanate, for example RNCO, in which R=$C_1$–$C_{10}$-alkyl and with phosgene to give a sulfonyl isocyanate of the formula (XI), and b) reacting the sulfonyl isocyanate formed, of the formula (XI), with an amino heterocycle of the formula (XII) to give the sulfonylurea; or a)

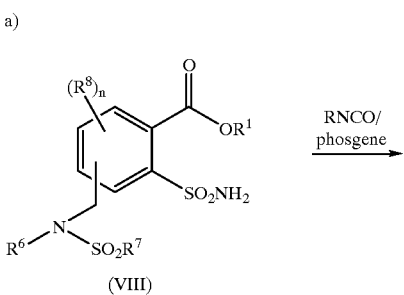

(VIII)

12) a) reacting a compound of the formula (VIII) with a carbonic acid derivative such as R—CO—OPh, in which Ph=unsubstituted or substituted phenyl and R=halogen or unsubstituted or substituted phenoxy to give a phenylsulfonyl carbamate of the formula (XIV), and b) reacting the phenylsulfonyl carbamate formed, of the formula (XIV), in which Ph=unsubstituted or substituted phenyl, with an amino heterocycle of the formula (XII) to give the sulfonylurea.

The symbols used in formulae (IX), (X), (XI), (XII), (XIII) and (XIV) have the same meaning as stated in formula (I), including the preferred ranges stated herefor; in addition, the following meanings are also used therein:

$R^x$, $R^y$ independently of one another are a hydrogen atom, halogen, $(C_1-C_4)$alkyl, $(C_1-C_4)$alkoxy, $(C_1-C_4)$alkylthio, where each of the last-mentioned 3 radicals is unsubstituted or substituted by one or more radicals selected from the group consisting of halogen, $(C_1-C_4)$alkoxy and $(C_1-C_4)$alkylthio, or are mono- or di[$(C_1-C_4)$alkyl]amino, $(C_2-C_6)$alkenyl, $(C_2-C_6)$alkynyl, $(C_3-C_6)$alkenyloxy or $(C_3-C_6)$alkynyloxy, X is CH or N, and Y is halogen such as fluorine, chlorine, bromine or iodine, preferably chlorine.

Preferred compounds of the formulae (XI), (XIII) and (XIV) are those in which the group —$CH_2$—$NR^6$—$SO_2$—$R^7$ is in the para position relative to the group —$COOR^1$.

Sulfonylureas such as the compounds of the formula (XIII) can form salts in which the hydrogen of the —$SO_2$—NH— group is replaced by an agriculturally suitable cation. Examples of these salts are metal salts, in particular alkali metal salts or alkaline earth metal salts, in particular sodium salts and potassium salts, or else ammonium salts or salts with organic amines. Likewise, salt formation can be effected by an addition reaction of an acid with basic groups, such as, for example, amino and alkylamino. Acids which are suitable for this purpose are strong inorganic and organic acids, for example HCl, HBr, $H_2SO_4$ or $HNO_3$. If the present description mentions sulfonylureas such as the compounds of the formula (XIII), this is also to be understood as including their salts in each case.

In process variant 8), the reaction of the sulfonyl halides (VII) is carried out with amino heterocycles of the formula (XII) and cyanates MOCN preferably with base catalysis in inert aprotic organic solvents such as ethyl acetate, tetrahydrofuran, toluene or acetonitrile between 0° C. and the boiling point of the solvent. Examples of suitable bases are organic amine bases, in particular pyridines such as pyridine or 3-methylpyridine.

In process variant 9), the reaction of the compounds of the formulae (VIII) and (IX) is carried out preferably with base catalysis in an inert organic solvent such as dichloromethane, acetonitrile, dioxane, tetrahydrofuran or ethyl acetate at between 0° C. and the boiling point of the solvent. Examples of bases which are used are $K_2CO_3$ or organic amine bases such as 1,8-diazabicyclo[5.4.0]undec-7-ene (DBU).

In process variant 10), the reaction of the compound of the formula (XII) is carried out with phosgene to give heterocyclyl isocyanates of the formula (X), for example in inert organic solvents such as ethyl acetate, dioxane or aromatic solvents such as chlorobenzene, if appropriate with addition of an organic amine base such as triethylamine, in general between 0° C. and the boiling point of the solvent. The subsequent reaction of the compound of the formula (X) with the compound of the formula (VIII) is carried out for example in inert solvents such as ethyl acetate, dioxane or aromatic solvents such as chlorobenzene, preferably in the presence of bases such as $K_2CO_3$ or trialkylamines such as triethylamine or tributylamine, in general at temperatures of from −20° C. to the boiling point of the solvent (cf. for example, EP-A-232 067 or EP-A-166516).

In process variant 11), the reaction of the compound of the formula (VIII) is carried out with an alkyl isocyanate and phosgene to give phenylsulfonyl isocyanates of the formula (XI), for example in inert solvents such as dichloromethane, acetonitrile, dioxane, tetrahydrofuran, toluene or chlorobenzene, in general at temperatures of from 20° C. to the boiling point of the solvent. The subsequent reaction of the compound of the formula (XI) with amino heterocycles of the formula (XII) is carried out for example in inert solvents such as dichloromethane, acetonitrile, dioxane, tetrahydrofuran, toluene or chlorobenzene, in general at temperatures of from 0° C. to the boiling point of the solvent (cf. for example U.S. Pat. No. 4,481,029).

In process variant 12), the reaction of the compound of the formula (VIII) with a carbonic acid derivative, for example diphenyl carbonate or phenyl chloroformate, to give a phenylsulfonyl carbamate of the formula (XIV) is carried out for example in inert solvents such as xylene, dichloromethane, acetonitrile, dioxane, tetrahydrofuran, toluene or chlorobenzene, preferably in the presence of a base such as $K_2CO_3$ or organic amine bases such as triethylamine, preferably at temperatures of from 20° C. to the boiling point of the solvent (cf., for example, U.S. Pat. No. 4,684,393 and U.S. Pat. No. 4,743,290). The subsequent reaction of the compound of the formula (XIV) with amino heterocycles of the formula (XII) is carried out for example in inert solvents such as xylene, dichloromethane, acetonitrile, dioxane, tetrahydrofuran, toluene or chlorobenzene, in general at temperatures of between 20° C. and the boiling point of the solvent.

The compounds of the formula (I) according to the invention thus make possible an efficient preparation of herbicidal sulfonylureas and other active substances.

EXAMPLES

Example 1 a) 3-Amino-4-methoxycarbonylbenzylammonium chloride

After addition of 365 ml of concentrated hydrochloric acid (4.37 mol) and 9 g of $PtO_2$, a suspension of 900 g (4.37 mol) of methyl 4-cyano-2-nitrobenzoate in 13.5 l of methanol is first hydrogenated at room temperature at a hydrogen pressure of 1 bar. After the hydrogen uptake has subsided, the pressure is increased to 17 bar, and hydorgenation is continued until the hydrogen uptake is complete. For work-up, the pressure is released to atmospheric pressure, the catalyst is removed by filtration through silica gel and the filtrate is concentrated completely in vacuo. Digestion of the residue with ethyl acetate yields 3-amino-4-methoxycarbonylbenzylammonium chloride, yield 757 g (80%), melting point 185–190° C. (decomp.).

b) Methyl 2-amino-4-methanesulfonylaminomethylbenzoate 3 g of 3-amino4-methoxycarbonylbenzylammonium chloride (18.8 mmol) are dissolved in 50 ml of dimethylacetamide, triethylamine (2.8 g, 27.7 mmol) is added, and the mixture is subsequently reacted at 0–10° C. with a solution of methanesulfonyl chloride (1.6 g, 13.8 mmol) in 20 ml of dimethylacetamide. After 1 h, the solvent is removed in vacuo and the residue is worked up by extraction with water/dichloromethane. The combined organic extracts are washed with water and dried ($Na_2SO_4$) and then evaporated on a rotary evaporator. The residue obtained is crystallized from water, whereupon 3 g (84%) of methyl 2-amino-4-methanesulfonylaminomethylbenzoate of melting point 120–121° C. are obtained.

c) Methyl 2-chlorosulfonyl-4-methanesulfonylaminomethylbenzoate

After addition of 5 ml of glacial acetic acid, a solution of 3 g (11.6 mmol) of methyl 2-amino-4-methanesulfonylaminomethylbenzoate in 20 ml of concentrated hydrochloric acid is treated at 0–5° C. over 0.5 h with an aqueous $NaNO_2$ solution (0.81 g, 11.7 mmol, 10 ml of water), and stirring is continued for 0.5 h at 5° C. In parallel, 0.34 g (3.5 mmol) of CuCl is suspended in 30 ml of glacial acetic acid which had previously been saturated with $SO_2$ gas, and the mixture was subsequently treated with 30 ml of toluene. The diazonium salt solution which had been prepared beforehand is added dropwise to this mixture at 35° C. over 0.5 h, with the evolution of gas starting spontaneously. After 1 hour, the mixture is treated with water, the phases are separated and the aqueous phase is reextracted with dichloromethane. The combined organic phases are washed, dried ($Na_2SO_4$) and concentrated in vacuo. Extracting the residue by stirring with toluene yields 2.5 g (63%) of methyl 2-chlorosulfonyl-4-methanesulfonylaminomethylbenzoate of melting point 93–94° C.

d) Methyl 2-sulfamoyl-4-methanesulfonylaminomethylbenzoate

A solution of 11 g (32 mmol) of methyl 2-chlorosulfonyl-4-methanesulfonylaminomethylbenzoate in 200 ml of THF is treated at 0° C. with 1.1 g (64 mmol) of $NH_3$ gas. For work-up, the mixture is concentrated in vacuo. Extracting the residue by stirring with water and then filtration and drying in vacuo give 8.3 g (80%) of methyl 2-sulfamoyl-4-methanesulfonylaminomethylbenzoate of melting point 185–187° C.

e) Methyl 2-[3-(4,6-dimethoxypyrimidin-2-yl) ureidosulfonyl]-4-methanesulfonaminomethylbenzoate 87.15 g (0.2677 mol) of methyl 2-sulfamoyl-4-methanesulfonylaminomethylbenzoate and 74.42 g (0.2677 mol) of N-(4,6-dimethoxypyrimidin-2-yl)phenylcarbamate are suspended in 600 ml of acetonitrile with ice-cooling at 5° C., and the mixture is treated with 40.4 ml (0.2677 mol) of 1,8-diazabicyclo[5.4.0]undec-7-ene in the course of 0.5 hours. After 2 hours at room temperature, approx. ⅔ of the solvent is removed in vacuo and the residue is stirred vigorously with 600 ml of 2N HCl and 400 ml of diisopropyl ether. The product which has precipitated is filtered off with suction, washed in succession with water and diisopropyl ether (in each case twice) and dried in vacuo. This gives 125 g of methyl 2-[3-(4,6-dimethoxypyrimidin-2-yl) ureidosulfonyl]-4-methanesulfonaminomethylbenzoate (92%) of melting point 191–193° C. (decomp.).

Example 2

3-Amino-4-methoxycarbonylbenzylammonium chloride 18.5 g (0.09 mol) of methyl 4-cyano-2-nitrobenzoate and 0.93 g of palladium hydroxide (20% on charcoal) are suspended in a mixture of 8 ml of concentrated hydrochloric acid (30% strength) and 315 ml of water in a Hastelloy stirred autoclave. Then, the mixture is hydrogenated at a hydrogen pressure of 17 bar until the hydrogen uptake is complete. After the pressure in the autoclave has been released and the catalyst filtered off, the filtrate is evaporated completely. This gives 19.5 g (97% strength) of 3-amino-4-methoxycarbonylbenzylammonium chloride of melting point 200–205° C.

Example 3
3-Amino-4-methoxycarbonylbenzylammonium chloride

In a stainless steel autoclave, 8.0 g of palladium hydroxide (20% on charcoal) and 100 ml of acetic acid are made inert with $N_2$. Then, a hydrogen pressure of 17 bar is applied. A solution of 300 g (1.455 mol) of methyl 2-nitro-4-cyanobenzoate in 2.6 l of acetic acid is then metered into the vigorously stirred mixture over 3 hours at +20° C. with cooling, using a metering pump. The $H_2$ pressure is kept at 17 bar. The pressure in the autoclave is released and the contents are made inert with $N_2$. The catalyst is filtered off and the filtrates are evaporated. Yield (acetate of the product): 91% of theory in the form of viscous residue. By dissolving the residue in toluene and passing in HCl gas (1 equivalent) at 0 to +10° C., a quantitative precipitate of 3-amino-4-methoxycarbonylbenzylammonium chloride is obtained, which is filtered off in the form of white crystals and dried (yield 91%, melting point 204–206° C.).

Example 4
a) 3-Nitro-4-methoxycarbonylbenzylammonium chloride 700 ml of a 1 M $BH_3$ solution in THF (0.7 mol) are metered in the course of one hour at 40–50° C. into a solution of 144 g (0.7 mol) of methyl 4-cyano-2-nitrobenzoate in 250 ml of THF and the mixture is subsequently refluxed for a further 1.5 hours. The reaction mixture is then treated with 600 ml of methanol saturated with hydrogen chloride gas, with ice-cooling, and refluxed for one hour. The mixture is concentrated completely under atmospheric pressure and reevaporated with 700 ml of methanol. The residue which remains is stirred with 500 ml of ethyl acetate and filtered, and the product is dried. This gives 115 g (67%) of 3-nitro-4-methoxycarbonylbenzylammonium chloride of melting point 247–248° C.

b) Methyl 4-methanesulfonylaminomethyl-2-nitrobenzoate 9.4 ml (0.244 mol) of methanesulfonyl chloride are metered over 30 minutes with ice-cooling to a solution of 30.1 g (0.122 mol) of 3-nitro-4-methoxycarbonyl-benzylammonium chloride and 34 ml (0.244 mol) of triethylamine in 300 ml of dichloromethane, and stirring of the mixture is continued for one hour. For work-up, the reaction mixture is treated with ice water, the phases are separated, and the aqueous phase is reextracted twice more with dichloromethane. After drying ($Na_2SO_4$), filtration and concentration, 31.3 g (89%) of methyl 4-methanesulfonylaminomethyl-2-nitrobenzoate remain as a syrupy oil.

c) Methyl 2-amino-4-methanesulfonylaminomethylbenzoate 13.25 g (46 mmol) of methyl 4-methanesulfonylaminomethyl-2-nitrobenzoate are dissolved in 200 ml of methanol. After addition of 1.4 ml (46 mmol) of concentrated hydrochloric acid and 1 g of Pd catalyst (10% on active charcoal), the mixture is hydrogenated with hydrogen under atmospheric pressure until the hydrogen uptake is complete. The hydrogen is removed from the catalyst by filtration and the filtrate is concentrated completely. Crystallization of the residue from water yields 10.4 g (88%) of methyl 2-amino-4-methanesulfonylaminomethylbenzoate of melting point 121–122° C.

We claim:
1. A compound of the formula (I),

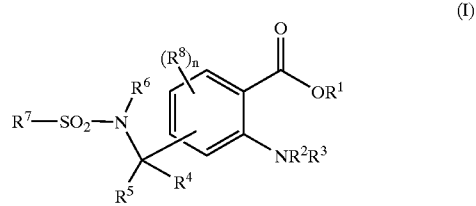

in which $R^1$ is H, $(C_1-C_8)$alkyl, $(C_3-C_8)$alkenyl or $(C_3-C_8)$alkynyl, where the last 3 radicals are unsubstituted or substituted, $R^2$, $R^3$ independently of one another are H or acyl, $R^4$, $R^5$ are H, $R^6$ is H or $(C_1-C_8)$alkyl which is unsubstituted or substituted, $R^7$ is $(C_1-C_8)$alkyl, $(C_3-C_8)$alkenyl, $(C_3-C_8)$alkynyl, $(C_6-C_{14})$aryl or mono- or di $(C_1-C_8)$alkylamino which are unsubstituted or substituted, or $R^6$ and $R^7$ together form a chain of the formula —$(CH_2)_m$—$B_{m1}$— which is unsubstituted or substituted, and where m=2, 3 or 4, m¹=0 or 1 and B=CO or $SO_2$, $R^8$ radicals are identical or different and are $(C_1-C_4)$alkyl, $(C_1-C_4)$alkoxy, [$(C_1-C_4)$alkyl]carbonyl or [$(C_1-C_4)$alkoxy]carbonyl which are unsubstituted or substituted, or $R^8$ is halogen, $NO_2$ or CN, and n is 0, 1, 2 or 3, wherein, unless otherwise identified, the substituents are halogen, $(C_1-C_8)$alkoxy, $(C_1-C_8)$haloalkoxy, $(C_1-C_8)$alkylthio, hydroxyl, amino, nitro, carboxyl, cyano, azido $(C_1-C_8)$alkoxycarbonyl, $(C_1-C_8)$alkylcarbonyl, formyl, carbamoyl, mono- and di-$(C_1-C_8)$ alkylaminocarbonyl, acylamino, mono- and di-$(C_1-C_8)$ alkylamino, $(C_1-C_8)$alkylsulfinyl, $(C_1-C_8)$haloalkylsulfinyl, $(C_1-C_8)$alkylsulfonyl, halo$(C_1-C_8)$alkylsulfonyl, $(C_1-C_8)$cycloalkyl, $(C_1-C_8)$ cycloalkenyl, wherein the cycloalkyl and cycloalkyl radicals are optionally substituted by $(C_1-C_8)$alkyl and halo$(C_1-C_8)$alkyl, $(C_1-C_8)$alkenyl, $(C_1-C_8)$alkynyl, $(C_1-C_8)$alkenyloxy or $(C_1-C_8)$alkynyloxy.

2. A compound of the formula (I) as claimed in claim 1, where $R^1$ is H or $(C_1-C_4)$alkyl, preferably $(C_1-C_4)$alkyl, $R^2$, $R^3$ are H, $R^4$, $R^5$ are H, $R^6$ is H, $R^7$ is $(C_1-C_4)$alkyl, and n is 0.

3. A compound of the formula (I) as claimed in claim 1, in which the group —$CR^4R^5$—$NR^6$—$SO_2$—$R^7$ is in the para position relative to the group —CO—$OR^1$.

4. A process for the preparation of a compound of the formula (I) as claimed in claim 1, comprising the steps of:

1a) reacting a compound of the formula (II)

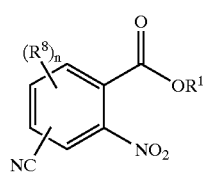
(II)

by catalytic hydrogenation in the absence of an acid to give a compound of the formula (III) or by catalytic hydrogenation in the presence of an acid $H^+X^-$, where $X^-$ is an equivalent of an acid anion, to give a compound of the formula (IIIa), where $X^-$ is an equivalent of an acid anion,

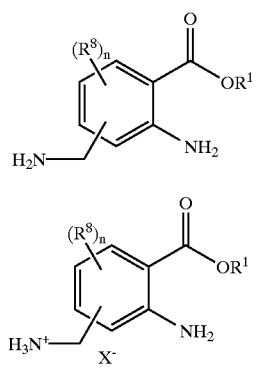

(III)

(IIIa)

and subsequently
   1b) reacting the compound of the formula (III) or (IIIa) with a sulfonic acid derivative to give a compound of the formula (I) where $R^2$, $R^3$ and $R^6$=H; or
2a) α) reacting a compound of the formula (II)

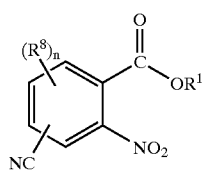
(II)

with a reagent that reduces a nitro group to an amine to give a compound of the formula (IV),

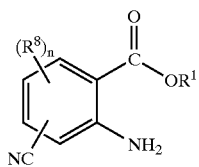
(IV)

and subsequently
   (β) reacting the compound of the formula (IV) either by catalytic hydrogenation or with a reagent that reduces a nitrile to an amine to give a compound of the formula (III) or (IIIa),
and subsequently
   2b) reacting the compound of the formula (III) or (IIIa) with a sulfonic acid derivative to give a compound of the formula (I) where $R^2$, $R^3$ and $R^6$=H; or 3a) α) reacting a compound of the formula (II)

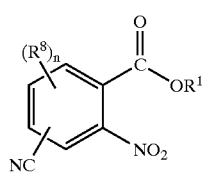
(II)

with a reagent that reduces a nitrile to an amine to give a compound of the formula (V) or (Va), where $X^-$ is as defined in formula (IIIa),

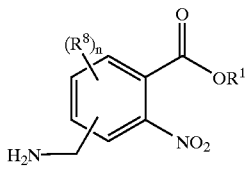
(V)

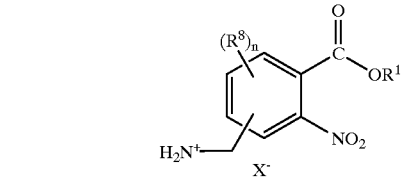
(Va)

and subsequently
   (β) reacting the compound of the formula (V) or (Va) with a reagent that reduces a nitro group to an amine or by catalytic hydrogenation to give a compound of the formula (III) or (IIIa), and subsequently
   3b) reacting the compound of the formula (III) or (IIIa) with a sulfonic acid derivative to give a compound of the formula (I) where $R^2$, $R^3$ and $R^6$=H; or
4a) α) reacting a compound of the formula (II)

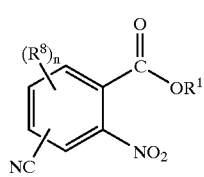
(II)

with a reagent that reduces a nitrile to an amine to give a compound of the formula (V) or (Va), where $X^-$ is as defined in formula (IIIa),

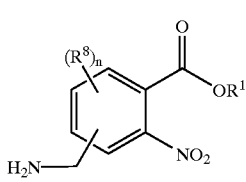
(V)

-continued (Va)

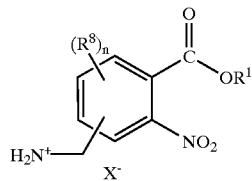

(β) and subsequently reacting the compound of the formula (V) or (Va) with a sulfonic acid derivative to give a compound of the formula (VI), (VI)

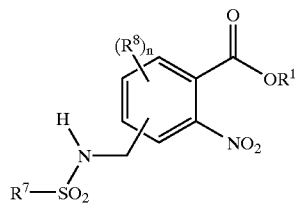

and subsequently 4b) reacting the compound of the formula (VI) with a reagent that reduces a nitro group to an amine or by catalytic hydrogenation to give a compound of the formula (I) where $R^2$, $R^3$ and $R^6$=H, where $R^1$, $R^7$, $R^8$ and n in formulae (II), (III), (IIIa), (IV), (V), (Va) and (VI) are as defined in formula (I) in claim 1; and optionally subsequently 5) reacting the compound of the formula (I) obtained in one of steps 1)–4) with an alkylating agent or by reductive amination to give a compound of the formula (I) where $R^6$=unsubstituted or substituted $C_1$–$C_8$-alkyl, or with an acylating agent to give a compound of the formula (I) where $R^2$ and/or $R^3$=acyl. xxxxxxx 5. A process for the preparation of a compound of the formula (XIII), in which $R^1$, $R^6$, $R^7$, $R^8$ and n are as defined in formula (I) in claim 1, $R^x$, $R^y$ independently of one another are a hydrogen atom, halogen, $(C_1$–$C_4)$alkyl, $(C_1$–$C_4)$alkoxy, $(C_1$–$C_4)$alkylthio, where each of the last-mentioned 3 radicals is unsubstituted or substituted by one or more radicals selected from the group consisting of halogen, $(C_1$–$C_4)$alkoxy and $(C_1$–$C_4)$alkylthio, or are mono- or di[$(C_1$–$C_4)$alkyl]amino, $(C_2$–$C_6)$alkenyl, $(C_2$–$C_6)$alkynyl, $(C_3$–$C_6)$alkenyloxy or $(C_3$–$C_6)$alkynyloxy, and X is CH or N, (XIII)

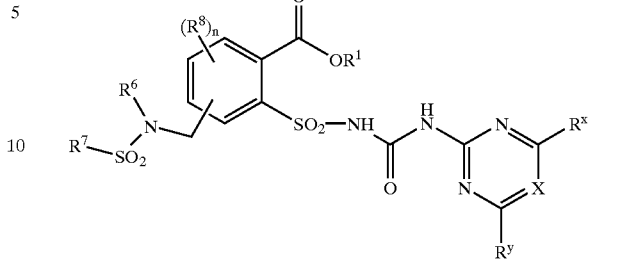

comprising the steps of

A) preparing a compound of the formula (I) as defined in claim 1, where $R^2$ and $R^3$=H, by 1a) reacting a compound of the formula (II)

(II)

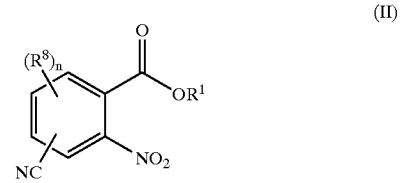

by catalytic hydrogenation in the absence of an acid to give a compound of the formula (III) or by catalytic hydrogenation in the presence of an acid $H^+X^-$, where $X^-$ is an equivalent of an acid anion, to give a compound of the formula (IIIa), where $X^-$ is an equivalent of an acid anion, (III)

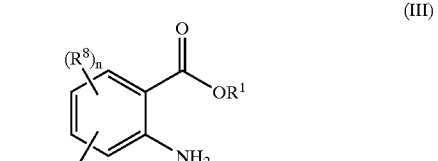

(IIIa)

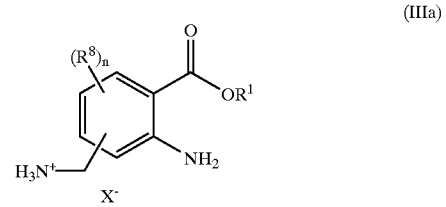

and subsequently 1b) reacting the compound of the formula (III) or (IIIa) with a sulfonic acid derivative to give a compound of the formula (I) where $R^2$, $R^3$, and $R^6$=H; or 2a) α) reacting a compound of the formula (II)

(II)

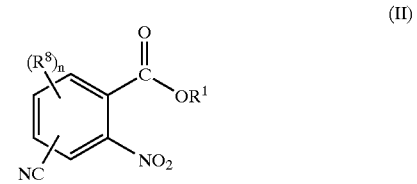

with a reagent that reduces a nitro group to an amine to give a compound of the formula (IV),

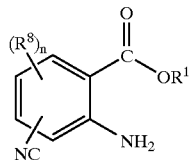
(IV)

and subsequently

β) reacting the compound of the formula (IV) either by catalytic hydrogenation or with a reagent that reduces a nitrile to an amine to give a compound of the formula (III) or (IIIa), and subsequently 2b) reacting the compound of the formula (III) or (IIIa) with a sulfonic acid derivative to give a compound of the formula (I) where $R^2$, $R^3$ and $R^6$=H; or 3a) α) reacting a compound of the formula (II)

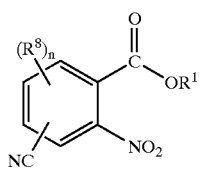
(II)

with a reagent that reduces a nitrile to an amine to give a compound of the formula (V) or (Va), where X⁻ is as defined in formula (IIIa),

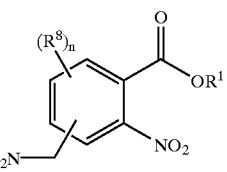
(V)

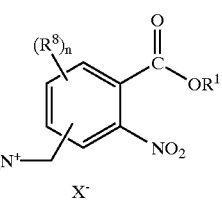
(Va)

and subsequently

β) reacting the compound of the formula (V) or (Va) with a reagent that reduces a nitro compound to an amine or by catalytic hydrogenation to give a compound of the formula (III) or (IIIa), and subsequently 3b) reacting the compound of the formula (III) or (IIIa) with a sulfonic acid derivative to give a compound of the formula (I) where $R^2$, $R^3$ and $R^6$=H; or 4a) α) reacting a compound of the formula (II)

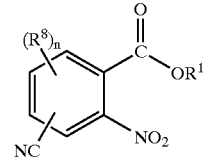
(II)

with a reagent that reduces a nitro compound to an amine to give a compound of the formula (V) or (Va), where X⁻ is as defined in formula (IIIa),

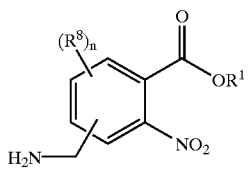
(V)

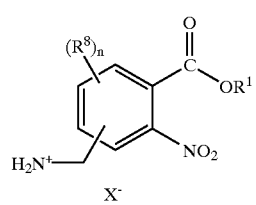
(Va)

β) and subsequently reacting the compound of the formula (V) or (Va) with a sulfonic acid derivative to give a compound of the formula (VI),

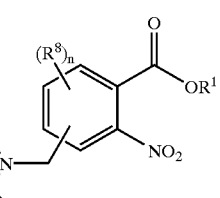
(VI)

and subsequently 4b) reacting the compound of the formula (VI) with a reagent that reduces a nitro compound to an amine or by catalytic hydrogenation to give a compound of the formula (I) where $R^2$, $R^3$ and $R^6$=H;

where $R^1$, $R^7$, $R^8$ and n in formulae (II), (III), (IIIa), (IV), (V), (Va) and (VI) are as defined in formula (I) in claim 1; and optionally subsequently 5) reacting the compound of the formula (1) which has been obtained in one of steps A1)–A4) with an alkylating agent or by reductive amination to give a compound of the formula (1) where $R^6$=unsubstituted or substituted $C_1$–$C_8$alkyl; and subsequently B) preparing a compound of the formula (VII) by 6) reacting the compound of the formula (I) which has been obtained in step A) to give a compound of the formula (VII), (VII)

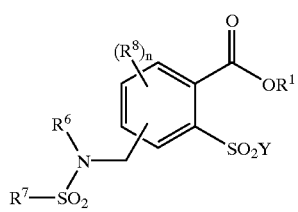

the compound of the formula (1) being reacted in the presence of an acid with a diazotizing agent and subsequently with an SO₂ source in the presence of a copper catalyst and an acid, where $R^1$, $R^6$, $R^7$, $R^8$ and n in formula (VII) are as defined in formula (1) in claim 1 and Y=halogen; and subsequently C) preparing the compound of the formula (XIII) by C1) reacting the compound of the formula (VII) which has been obtained in step B6) with an amine of the formula (XII) in the presence of MOCN, wherein M is an ammonium ion or an alkali metal ion, to give a compound of the formula (XIII); or (XII)

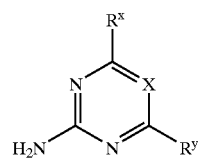

C2.1) preparing a compound of the formula (VIII) by 7) reacting the compound of the formula (VII) which has been obtained in step B6) to give a compound of the formula (VIII), (VIII)

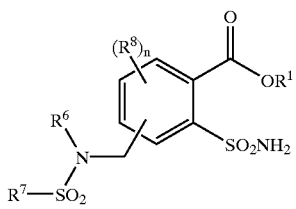

the compound of the formula (VIII) being subjected to aminolysis with ammonia in a suitable solvent, where $R^1$, $R^6$, $R^7$, $R^8$ and n in formula (VIII) are as defined in formula (1) in claim 1;

and subsequently

C2.2) preparing the compound of the formula (XIII) by 9) reacting the compound of the formula (VIII) with a compound of the formula (IX) to give the compound of the formula (XIII); or (IX)

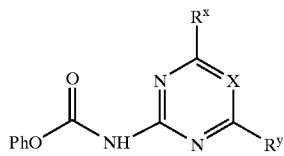

10) reacting the compound of the formula (VIII) with an isocyanate of the formula (X) to give the compound of the formula (XIII); or (X)

O=C=N—[triazine ring with $R^x$, X, $R^y$]

11) reacting the compound of the formula (VIII) with an alkyl isocyanate and phosgene to give a compound of the formula (XI), (XI)

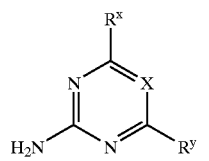

which is subsequently reacted with an amine of the formula (XIII) to give the compound of the formula (XIII); or (XII)

[triazine ring $H_2N$, $R^x$, X, $R^y$]

12) reacting the compound of the formula (VIII) with a carbonic acid derivative R—CO—OPh, in which Ph=unsubstituted or substituted phenyl and R=halogen or unsubstituted or substituted phenoxy to give a compound of the formula (XIV), (XIV)

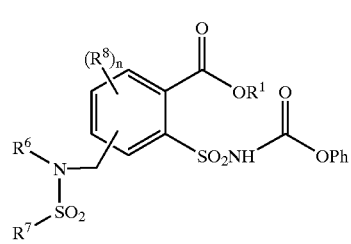

which is subsequently reacted with an amine of the formula (XII) to give the compound of the formula (XIII);

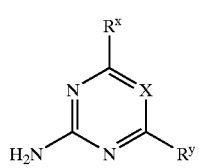
(XII)

where $R^1$, $R^7$, $R^8$, and n in formulae (XI) and (XIV) are as defined in formula (1) in claim 1, $R^x$, $R^y$ and X in formulae (IX), (X) and (XII) are as defined in formula (XIII) of the present claim and Ph in formulae (IX) and (XIV) is unsubstituted or substituted phenyl, wherein the substituents on the phenyl ring are halogen, $(C_1-C_8)$alkoxy, $(C_1-C_8)$haloalkoxy, $(C_1-C_8)$alkylthio, hydroxyl, amino, nitro, carboxyl, cyano, azido $(C_1-C_8)$ alkoxycarbonyl, $(C_1-C_8)$alkylcarbonyl, formyl, carbamoyl, mono- and di -$(C_1-C_8)$ alkylaminocarbonyl, acylamino, mono- and di-$(C_1-C_8)$ alkylamino, $(C_1-C_8)$alkylsulfinyl, $(C_1-C_8)$haloalkylsulfinyl, $(C_1-C_8)$alkylsulfonyl, halo $(C_1-C_8)$alkylsulfonyl, $(C_1-C_8)$cycloalkyl, $(C_1-C_8)$ cycloalkenyl, wherein the cycloalkyl and cycloalkyl radicals are optionally substituted by $(C_1-C_8)$alkyl and halo$(C_1-C_8)$ alkyl, $(C_1-C_8)$alkenyl, $(C_1-C_8)$alkynyl, $(C_1-C_8)$alkenyloxy or $(C_1-C_8)$alkynyloxy.

6. A process for the preparation of a compound of the formula (XIII) as defined in claim 5,

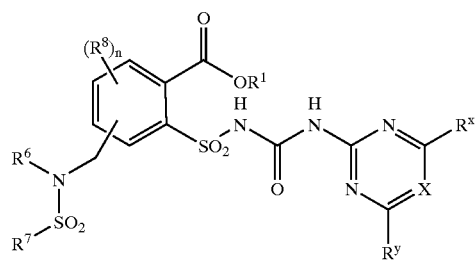
(XIII)

comprising steps B) and C1) or B), C2.1) and C2.2) as defined in claim 5.

7. A process for the preparation of a compound of the formula (VII) as defined in claim 5,

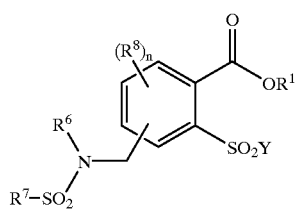
(VII)

wherein
a compound of the formula (I) as defined in claim 1 and in which $R^2$, $R^3$=H is diazotized in the presence of an acid and subsequently reacted with an $SO_2$ source in the presence of a copper catalyst and an acid.

8. A process for the preparation of a compound of the formula (VIII) as defined in claim 5,

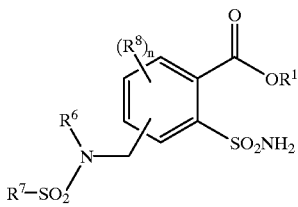
(VIII)

comprising the steps of

A) reacting a compound of the formula (I) as defined in claim 1 and in which $R^2$, $R^3$=H to give a compound of the formula (VII),

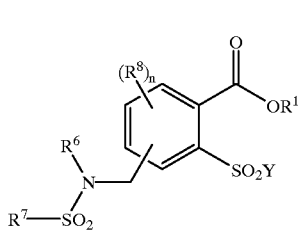
(VII)

wherein the compound of the formula (I) is diazotized in the presence of an acid and subsequently reacted with an $SO_2$ source in the presence of a copper catalyst and of an acid, and subsequently B) reacting the compound of the formula (VII) to give a compound of the formula (VIII),

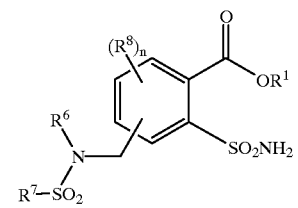
(VIII)

wherein the compound of the formula (VIII) is subjected to aminolysis in a suitable solvent with ammonia.

9. A compound of the formula (Z') or (Za')

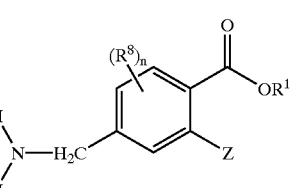
(Z)

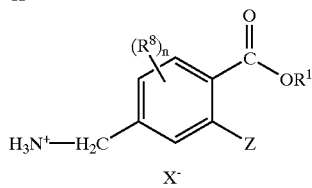
(Za)

in which
- $R^1$ is H, $(C_1-C_8)$alkyl, $(C_3-C_8)$alkenyl or $(C_3-C_8)$alkynyl, where the last 3 radicals are unsubstituted or substituted,
- $R^8$ radicals are identical or different and are $(C_1-C_4)$alkyl, $(C_1-C_4)$alkoxy, $[(C_1-C_4)$alkyl]carbonyl or $[(C_1-C_4)$alkyl]carbonyl which are unsubstituted or substituted, or $R^8$ is halogen, $NO_2$ or CN,
- n is 0, 1, 2 or 3,
- $X^-$ is an equivalent of an acid anion
- Z is $NH_2$ or $NO_2$
- and $R^1$ is not H if Z is $NO_2$ wherein, unless otherwise identified, the substituents are halogen, $(C_1-C_8)$alkoxy, $(C_1-C_8)$haloalkoxy, $(C_1-C_8)$alkylthio, hydroxyl, amino, nitro, carboxyl, cyano, azido $(C_1-C_8)$alkoxycarbonyl, $(C_1-C_8)$alkylcarbonyl, formyl, carbamoyl, mono- and di-$(C_1-C_8)$dialkylaminocarbonyl, acylamino, mono- and di-$(C_1-C_8)$ alkylamino, $(C_1-C_8)$alkylsulfinyl, $(C_1-C_8)$haloalkylsulfinyl, $(C_1-C_8)$alkylsulfonyl, halo$(C_1-C_8)$alkylsulfonyl, $(C_1-C_8)$cycloalkyl, $(C_1-C_8)$ cycloalkenyl, wherein the cycloalkyl and cycloalkyl radicals are optionally substituted by $(C_1-C_8)$ alkyl and halo$(C_1-C_8)$alkyl, $(C_1-C_8)$alkenyl, $(C_1-C_8)$alkynyl, $(C_1-C_8)$alkenyloxy or $(C_1-C_8)$alkynyloxy.

* * * * *